(12) United States Patent
Luttwak et al.

(10) Patent No.: US 11,666,361 B1
(45) Date of Patent: Jun. 6, 2023

(54) DEVICE AND METHOD FOR PHALANX FRACTURE REDUCTION

(71) Applicant: Rambam MedTech Ltd., Haifa (IL)

(72) Inventors: Ruth Luttwak, Binyamina (IL); Ophir Marko, Netanya (IL)

(73) Assignee: Rambam MedTech Ltd., Haifa (IL)

( * ) Notice: Subject to any disclaimer, the term of this patent is extended or adjusted under 35 U.S.C. 154(b) by 0 days.

(21) Appl. No.: 17/652,424

(22) Filed: Feb. 24, 2022

(51) Int. Cl.
A61B 17/62 (2006.01)
A61B 17/64 (2006.01)
A61B 17/66 (2006.01)
A61B 17/84 (2006.01)

(52) U.S. Cl.
CPC .......... *A61B 17/62* (2013.01); *A61B 17/6475* (2013.01); *A61B 17/66* (2013.01); *A61B 17/848* (2013.01)

(58) Field of Classification Search
CPC . A61B 17/17; A61B 17/1739; A61B 17/8897; A61B 17/66; A61B 17/62; A61B 17/848
USPC ................ 606/54–59, 96–98, 104, 53–59
See application file for complete search history.

(56) References Cited

U.S. PATENT DOCUMENTS

| | | | |
|---|---|---|---|
| 4,978,348 A | 12/1990 | Ilizarov | |
| 5,067,954 A | 11/1991 | Ilizarov | |
| 5,098,383 A * | 3/1992 | Hemmy | A61M 5/427 604/116 |
| 8,317,690 B2 * | 11/2012 | Ransden | A61B 17/3468 600/206 |
| 10,349,981 B2 | 7/2019 | Burgherr et al. | |
| 2012/0203061 A1 * | 8/2012 | Birk | A61F 5/0079 600/37 |
| 2014/0277450 A1 * | 9/2014 | Warburton | A61B 17/68 623/13.14 |
| 2016/0074049 A1 * | 3/2016 | Russell | A61B 17/8897 606/96 |
| 2016/0081727 A1 * | 3/2016 | Munday | A61B 17/7291 606/62 |
| 2016/0192975 A1 * | 7/2016 | Winnen | A61C 8/0012 606/300 |
| 2016/0235461 A1 | 8/2016 | Sumko | |

(Continued)

FOREIGN PATENT DOCUMENTS

CN 102836002 A 12/2012

OTHER PUBLICATIONS

An International Search Report and Written Opinion, dated Apr. 24, 2023, issued in PCT/IL2023/050188.

*Primary Examiner* — Eduardo C Robert
*Assistant Examiner* — Tara Rose E Carter
(74) *Attorney, Agent, or Firm* — Sughrue Mion, PLLC

(57) ABSTRACT

A guide device for an orthopedic surgery on a phalange includes a distal part having a pin guide is provided. The distal part includes a first opening having a first diameter at a proximal end for inserting at least a portion of a phalange into a tubular section of the distal part, and a second opening at a distal end. The pin guide is connected to the distal end, having a first length which is shorter than a length of a k-wire inserted into the phalange, and a second diameter which is greater than a diameter of the k-wire, and less than the first diameter. In certain embodiments the guide device further includes a proximal part having an aperture for inserting the phalange and a plurality of fasteners, for fastening the proximal part to the distal part.

20 Claims, 13 Drawing Sheets

(56) References Cited

U.S. PATENT DOCUMENTS

2017/0100273 A1\* 4/2017 McCormick .............. A61F 5/10
2021/0128136 A1   5/2021 Harari \* cited by examiner

DEVICE AND METHOD FOR PHALANX FRACTURE REDUCTION

TECHNICAL FIELD

The present disclosure relates generally to orthopedic surgical devices and specifically to fracture reduction through the distal phalanx.

BACKGROUND

Distal phalanx fractures are the most common type of fracture in the hand. When such a fracture occurs, a typical approach is to insert a Kirschner wire (also known as a k-wire) through the distal phalange in order to perform fixation of the bone. The k-wires, or pins, are sterilized, smooth stainless steel pins, and are widely used in reduction and fixations of fractures.

The distal phalange has a rounded tip, resulting in a risk of slippage of the k-wire, when inserted through the fingertip. Slippage can occur in the dorsal, lateral, or palmar direction, and is obviously unwanted, as it may injure surrounding tissue, and not achieve the purpose of the insertion, which is to fixate the bone in place.

In their surgical reference for K-wire Fixation, Fricker et al. recommend that a 16 gauge hypodermic needle, or a 1 mm drill guide be used to ensure proper insertion in order to prevent slippage. However, Fricker et al. recognize that at least one problem of this technique is that the k-wire may be inserted at an angle to the axis of the phalanx. This is likewise undesirable as it does not solve the problem of fixation, and if removed before a second k-wire is inserted, the second k-wire may slip and be placed along the wrong track.

It would therefore be advantageous to provide a solution that would overcome the challenges noted above.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include a method for performing k-wire fixation in a phalange. The method comprises: inserting a phalange into a first proximal part, the first proximal guide comprising an aperture through which to insert the phalange, and a plurality of fasteners; inserting the phalange into a distal part, the distal part comprising: a tubular section into which at least a portion of a distal phalanx of the phalange is inserted, and a pin guide; and inserting a k-wire through the pin guide and into the phalange.

Certain embodiments disclosed herein also include a guide device for an orthopedic surgery on a phalange, comprising: a distal part, having a first opening of a first diameter at a proximal end for inserting at least a portion of a phalange into a tubular section of the distal part, and a second opening at a distal end; and a pin guide connected to the distal end, the pin guide having a first length which is shorter than a length of a k-wire inserted into the phalange, and a second diameter which is greater than a diameter of the k-wire, and less than the first diameter.

In some embodiments disclosed herein the guide device further comprises a proximal part, the proximal part comprising: an aperture for inserting a phalange; and a plurality of fasteners, for fastening the proximal part to the distal part.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
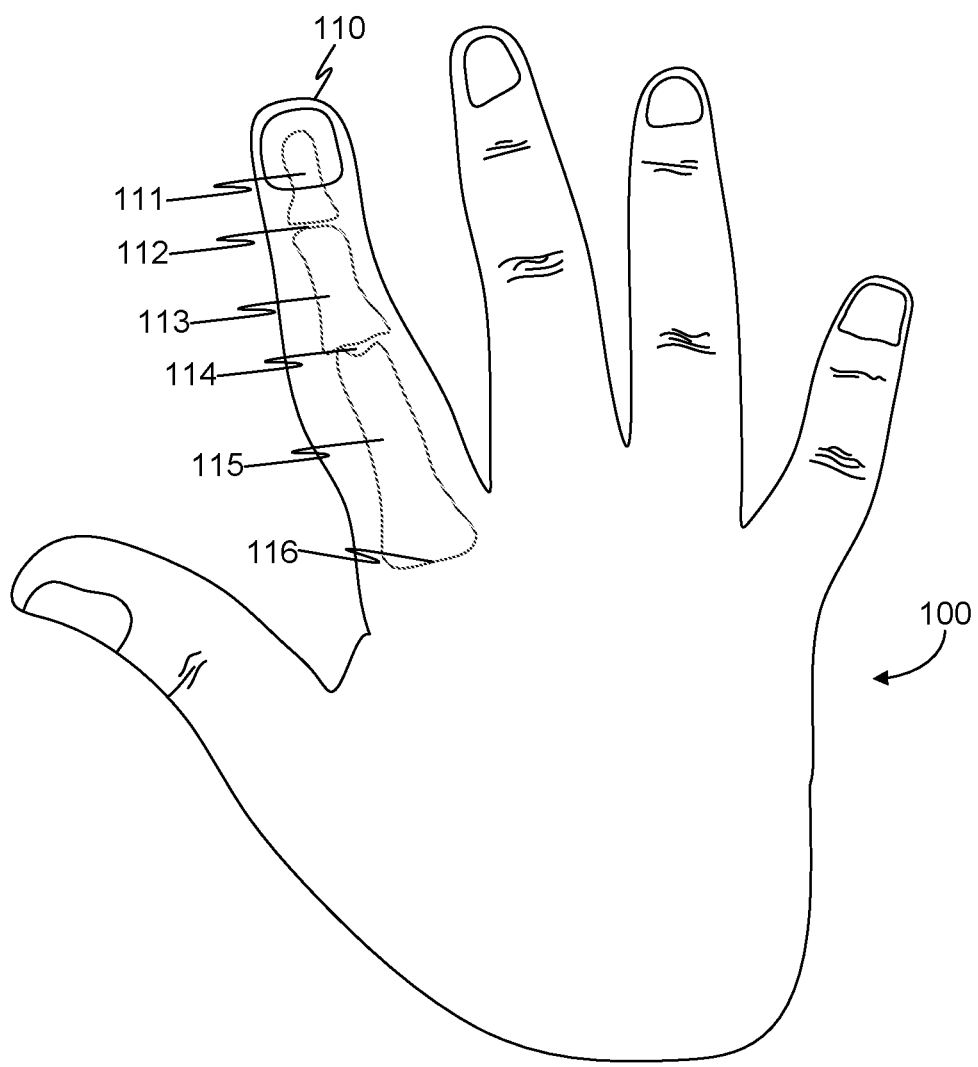
FIG. 1 is a diagram of a human right hand with a semi-transparent section corresponding to the index finger, in accordance with an embodiment.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

The various example disclosed embodiments include an orthopedic guide for performing guided phalange fracture reduction and fixation with k-wire using an external guide device mounted on a fractured finger.

FIG. 1 is an example diagram of a human right hand 100 with a semi-transparent section corresponding to the index finger 110, in accordance with an embodiment. While the index finger 110 is shown, the teachings herein can be applied to any of the digits of either human hand, without departing from the scope of the present disclosure. The index finger 110, also referred to as a phalange or phalanx, includes three bone portions. The distal phalanx 111 is connected to the middle phalanx 113 at the distal interphalangeal (DIP) joint 112. The middle phalanx 113 is connected to the proximal phalanx 115 at the proximal interphalangeal (PIP) joint 114. The proximal phalanx 115 is connected to a metacarpal bone (not shown) at the metacarpophalangeal (MCP) joint 116.

Figure 2A:
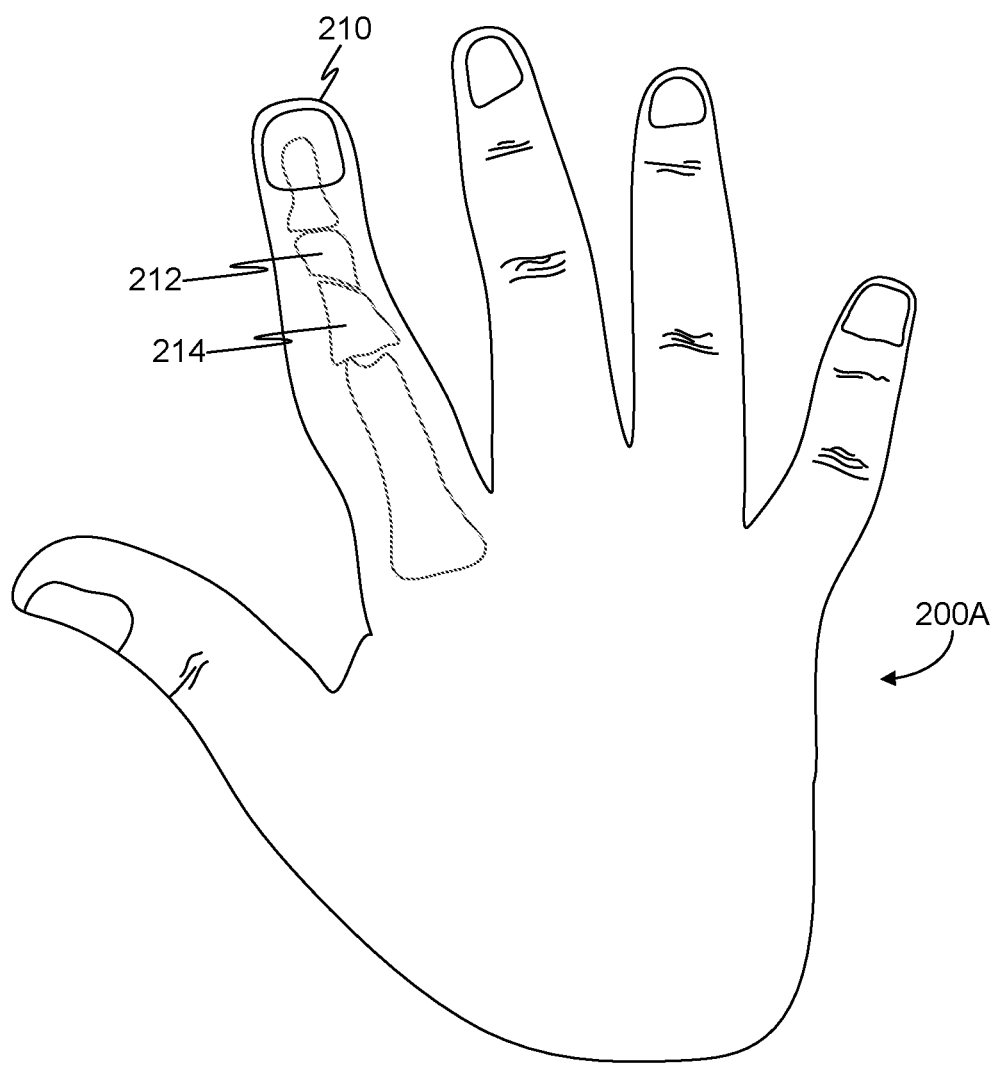
FIG. 2A is a diagram of a human right hand with a semi-transparent section corresponding to an index finger showing a middle phalanx fracture, in accordance with an embodiment.

FIG. 2A is an example diagram of a human right hand 200A with a semi-transparent section corresponding to an index finger 210 showing a middle phalanx fracture, in accordance with an embodiment. A middle phalanx exhibits a transverse fracture, such that the middle phalanx is fractured into a first portion 212 and a second portion 214. In order to fix in place the first portion 212 and the second portion 214, a k-wire may be inserted through the distal tip of the index finger 210, through the distal phalanx 211, through the DIP joint, through the first portion 212 to the second portion 214, up to the PIP joint and even beyond to the MCP joint, in certain embodiments.

Figure 2B:
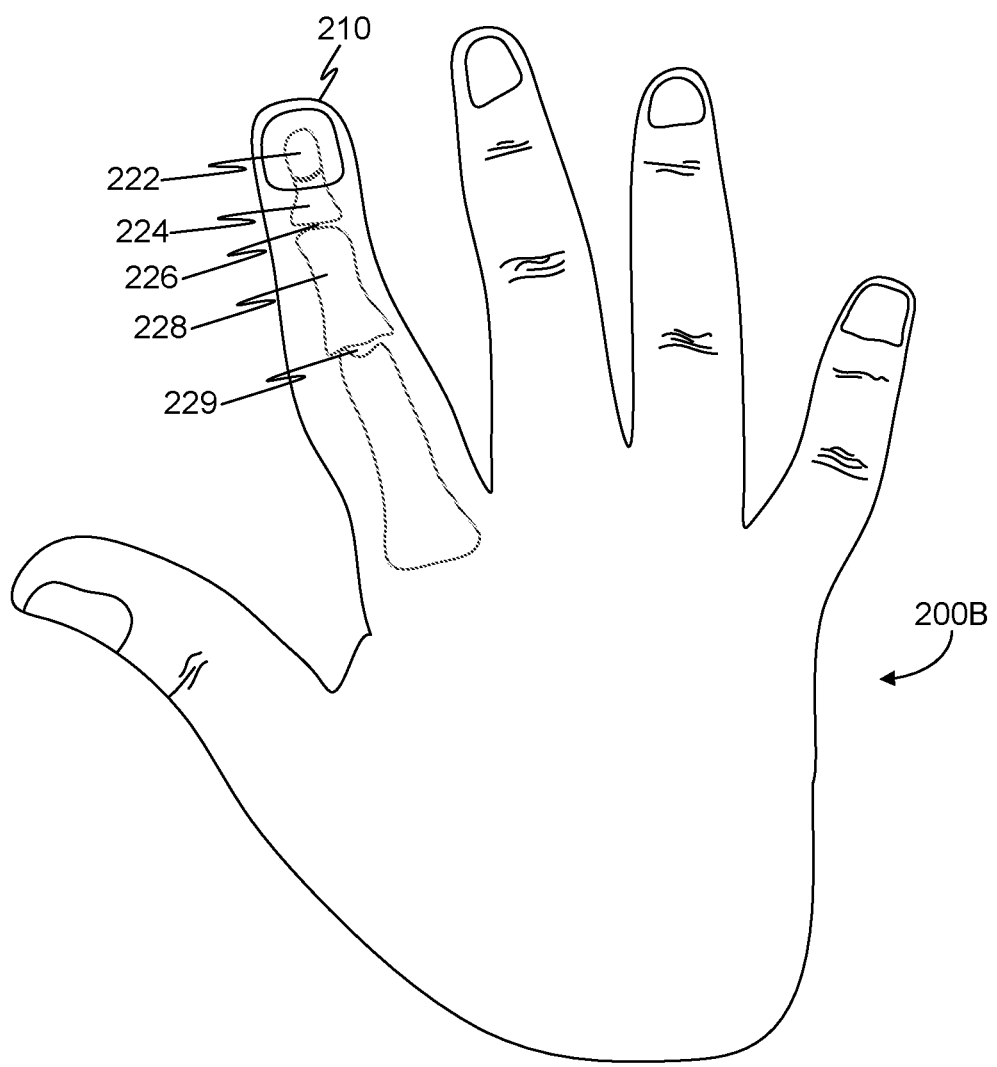
FIG. 2B is a diagram of a human right hand with a semi-transparent section corresponding to an index finger showing a distal phalanx fracture, in accordance with an embodiment.

FIG. 2B is an example diagram of a human right hand 200B with a semi-transparent section corresponding to an index finger 210 showing a distal phalanx fracture, in accordance with an embodiment. A distal phalanx exhibits a transverse fracture into two portions, a first portion 222 closer to the fingertip, and a second portion 224 closer to the DIP joint 226. In order to fix in place the first portion 222 to the second portion 224, a k-wire may be inserted by dissecting the subcutaneous tissues at fingertip, horizontal to the distal phalanx. In certain embodiments, for example when the fracture is proximal to the DIP joint 226, a k-wire may be further inserted through the DIP joint 226 into the middle phalanx 228 and up to the PIP joint 229. This may result in a more stable fixation, as the middle phalanx 228 provides additional support.

Figure 3:
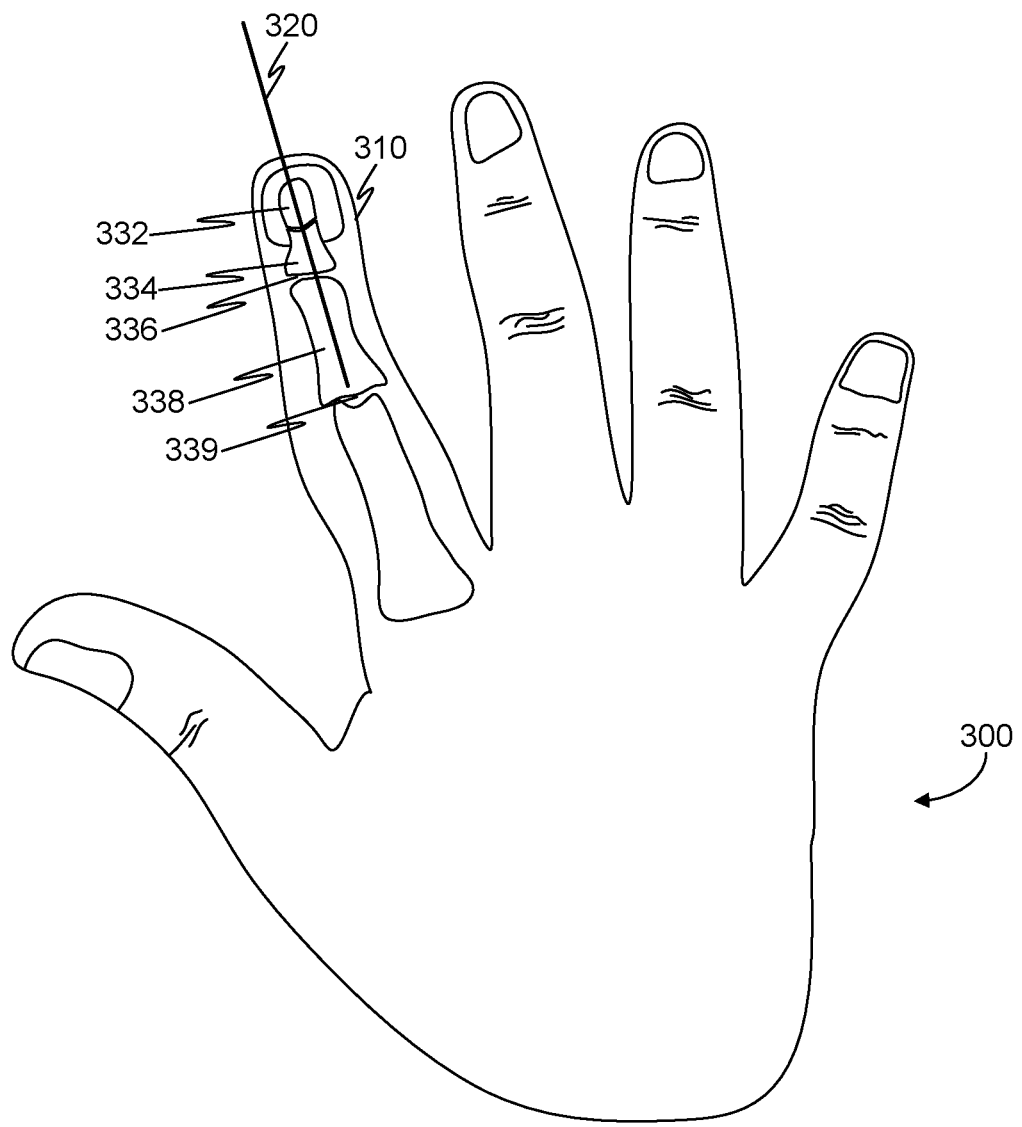
FIG. 3 is a diagram of a human right hand with a semi-transparent section corresponding to an index finger showing a distal phalanx fracture with a k-wire fixation, in accordance with an embodiment.

FIG. 3 is an example diagram of a human right hand 300 with a semi-transparent section corresponding to an index finger 310 showing a distal phalanx fracture with a k-wire fixation, in accordance with an embodiment. A distal phalanx exhibits a transverse fracture into two portions, a first portion 332 closer to the fingertip, and a second portion 334 closer to the DIP join 336. A k-wire 320 is inserted through the fingertip of the finger 310, through the first portion 332, the second portion 334, the DIP joint 336, and the middle phalanx 338, up to the PIP joint 339. Inserting the k-wire through the DIP joint 336 and into the middle phalanx 338 provides for an additional fixation in cases where the fracture is proximal to the DIP joint 336. Inserting the k-wire 320 properly through both bone fragments and the middle phalanx 338 is crucial for a successful recovery and repair. It is therefore important to be able to accurately guide the k-wire 320 when inserting, in order to remain centered across the anterior-posterior (AP) and lateral axes.

Figure 4:
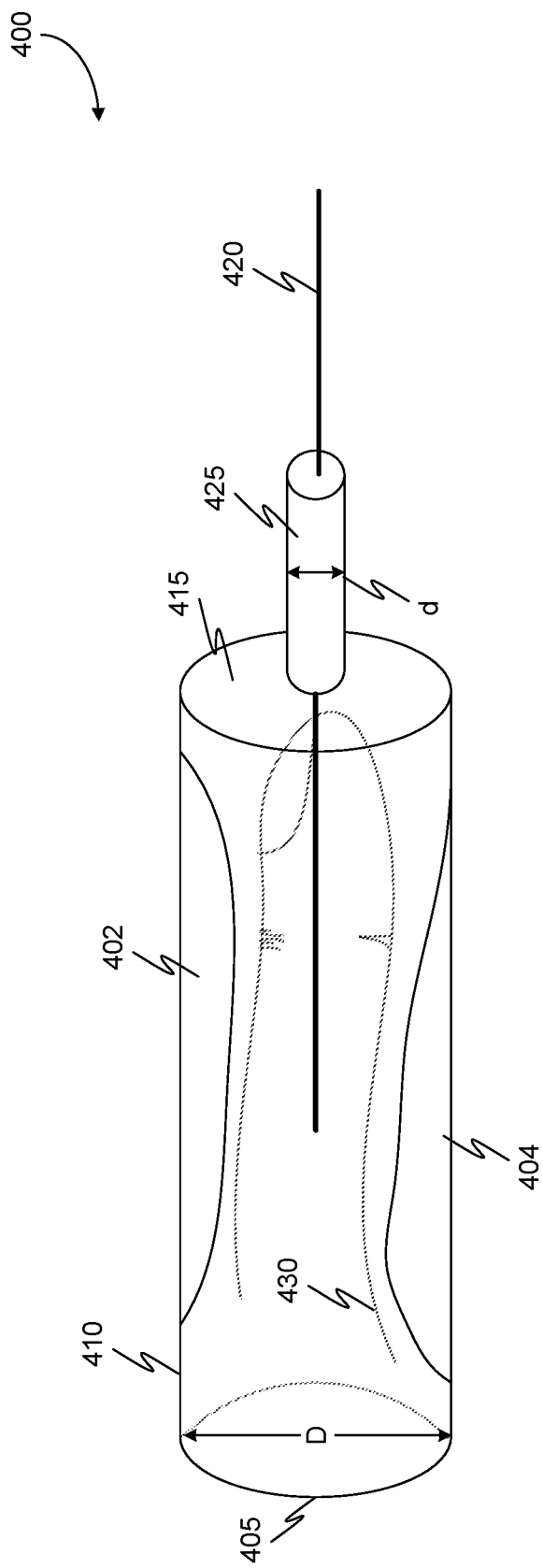
FIG. 4 is a diagram of a cross-section of a k-wire guide device, implemented in accordance with an embodiment.

FIG. 4 is an example diagram 400 of a cross-section of a k-wire guide device 410, implemented in accordance with an embodiment. In an embodiment the k-wire guide may be substantially tubular, having a length and a diameter. The k-wire guide 410 includes a proximal opening 405 through which a phalange may be inserted into an internal portion of the k-wire guide 410. The internal portion of the k-wire guide 410 may include at least a pressurizing device, such as a first inflatable cushion 402 which is diametrically opposite to a second inflatable cushion 404. In certain embodiments the internal portion may be tubular. In an embodiment, the first inflatable cushion 402 and second inflatable cushion 404 are connected to each other, or to a single pressure supply (not shown), in order to supply the same amount of pressure on the phalange 430 which is placed inside the k-wire guide 410. In certain embodiments, a single inflatable device is present in the k-wire guide 410, to create a uniform pressure field. Applying pressure on the phalange 430 serves to both keep the phalange in place through a friction fit, and to center the phalange within the k-wire guide 410, which has a diameter D (first diameter) which is greater than the diameter of the inserted phalange 430. In some embodiments, a sponge cushion may be used, such as a polyurethane foam. For example, a viscoelastic polyurethane foam may be used to hold a phalange in place.

The k-wire guide 410 further includes at a distal end 415 a pin guide 425. In an embodiment the pin guide 425 may be substantially tubular, having a length and a diameter. The pin guide 425 has a diameter d (second diameter) which is smaller than the diameter D at the proximal opening 405 of the k-wire guide 410. In an embodiment, the diameter d is larger in size than the diameter of a k-wire 420, so that the k-wire can pass through the pin guide 425 into the phalange 430. For example, the diameter d of the pin guide 425 may be 1 mm, within a 5% threshold. In an embodiment, the guide device may have a length between 1 cm and 7 cm. A length of k-wire should be longer than the length of the pin guide 425. In an embodiment, the length of the k-wire may be longer than the length of the pin guide 425 combined with the length of the k-wire guide 410.

In certain embodiments, a plurality of pin guides, such as pin guide 425, may be implemented. In some embodiments, at least a portion of the plurality of pin guides may further be implemented at an angle relative to a central pin guide.

Figure 5:
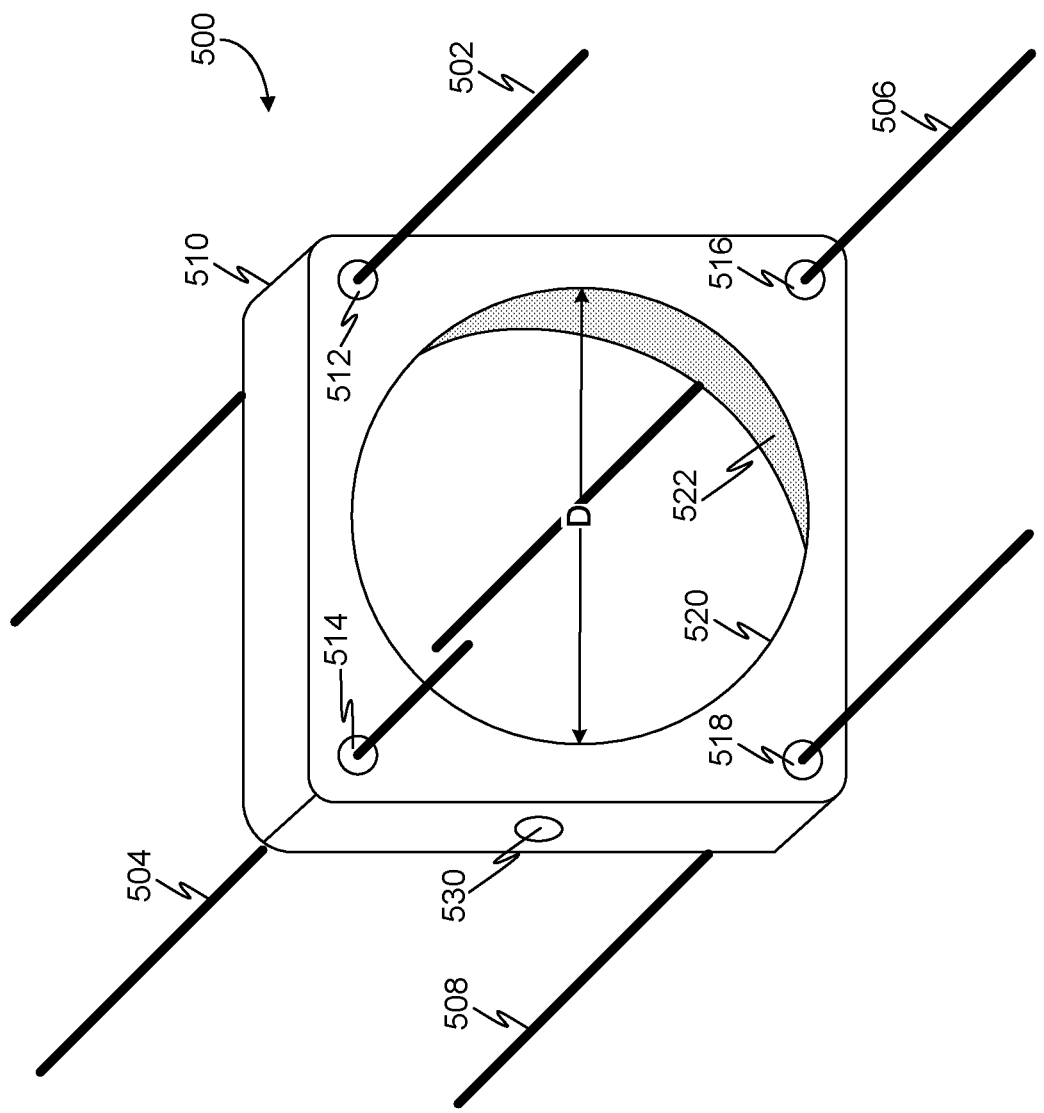
FIG. 5 is a diagram of a proximal part of a multi-part k-wire guide device, implemented in accordance with an embodiment.

FIG. 5 is an example diagram 500 of a proximal part 510 of a multi-part k-wire guide device, implemented in accordance with an embodiment. The multi-part k-wire guide device includes at least one proximal part 510, and a distal part, discussed in more detail in FIG. 6 below. In certain embodiments, a plurality of proximal parts may be utilized, for example in order to add stability to the fixation. The proximal part 510 includes a plurality of perforations, such a first perforation 512, second perforation 514, third perforation 516 and fourth perforation 518. In an embodiment, the perforations may be threaded. Each perforation allows a stabilizing rod to pass through, such that a first rod 502 can pass through the first perforation 512, a second rod 504 can pass through the second perforation 514, a third rod 506 can pass through the third perforation 516, and a fourth rod 508 can pass through the fourth perforation 518. In certain embodiments, the perforations may be smooth and the rods may be threaded. In such embodiment, the rods may be held in place to the proximal part 510 by affixing with a nut (not shown).

In certain embodiments, an anchor point can be utilized in place of a perforation. In certain embodiments, a combination of anchor points and perforations may be used. For example, an anchor point may be a threaded hole in the proximal part 510, into which a partially (or fully) threaded rod may be screwed in. This reduces the need for an additional fastener. In embodiments where a plurality of proximal parts are utilized, a first proximal part closest to the palm of the hand may include a plurality of anchor points to each of which a rod is fastened, while a second proximal part may include perforations which guide the second proximal part along the rods fastened to the first proximal part. In such embodiments, the diameter of the perforation of the second proximal part(s) may be larger than the diameter of the rods. Where a rod is fully threaded, the proximal part(s) may be held in place using, for example, nuts. The anchor points, rods, perforations, or a combination thereof, may be referred to generally throughout as a fastening system, which allows fastening a proximal part to at least a distal part.

The proximal part 510 further includes an aperture 520. In an embodiment, the aperture 520 is centered with respect to the proximal part 510. The aperture 520 has a diameter D which is large enough to allow a phalange to extend through the aperture 520. The aperture 520 has an internal surface 522, to which an inflatable member (not shown here, but discussed in more detail in FIG. 7), such as the inflatable cushion discussed above, may be affixed. A pressure supply (not shown) may be connected to the inflatable member through a duct 530 to supply and reduce pressure onto the phalange inserted in the aperture 520 as needed.

Figure 6:
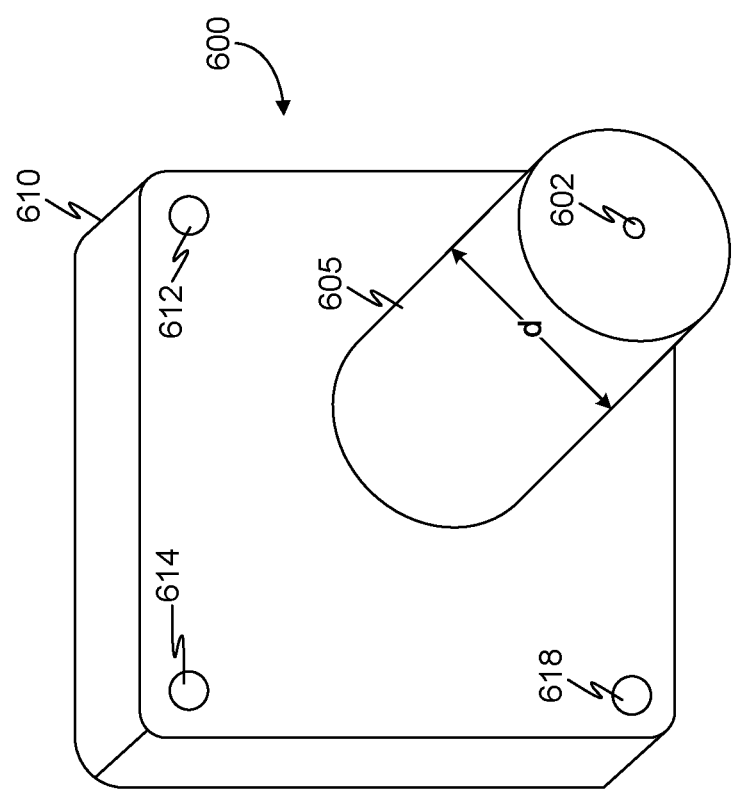
FIG. 6 is a diagram of a distal part of a multi-part k-wire guide device, implemented in accordance with an embodiment.

FIG. 6 is an example diagram 600 of a distal part 610 of a multi-part k-wire guide device, implemented in accordance with an embodiment. The multi-part k-wire guide device includes at least one proximal part, discussed in more detail in FIG. 5 above, and a distal part 610. The distal part 610 is operative to be placed such that the proximal part is closer to the proximal part of an inserted phalange and the distal part 610 is placed at the distal end of the inserted phalange of the proximal part 510 and further inserted through the first perforation 612 of the distal part 610.

The distal part 610 further includes a pin guide 605, through which a k-wire may be inserted at an opening 602. In certain embodiments, the pin guide 605 may have a diameter d which is less than the diameter D of the aperture 520, but greater than a diameter of the opening 602. This may be useful to create a friction fit to the distal tip of the inserted phalange. In some embodiments, the diameter of the opening 602 may be equal to the diameter d of the pin guide 605. The diameter of the opening 602 may be, for example 1 mm with a tolerance of 5%. In an embodiment, the distal part may have a length of 1 cm to 7 cm.

Figure 7A:
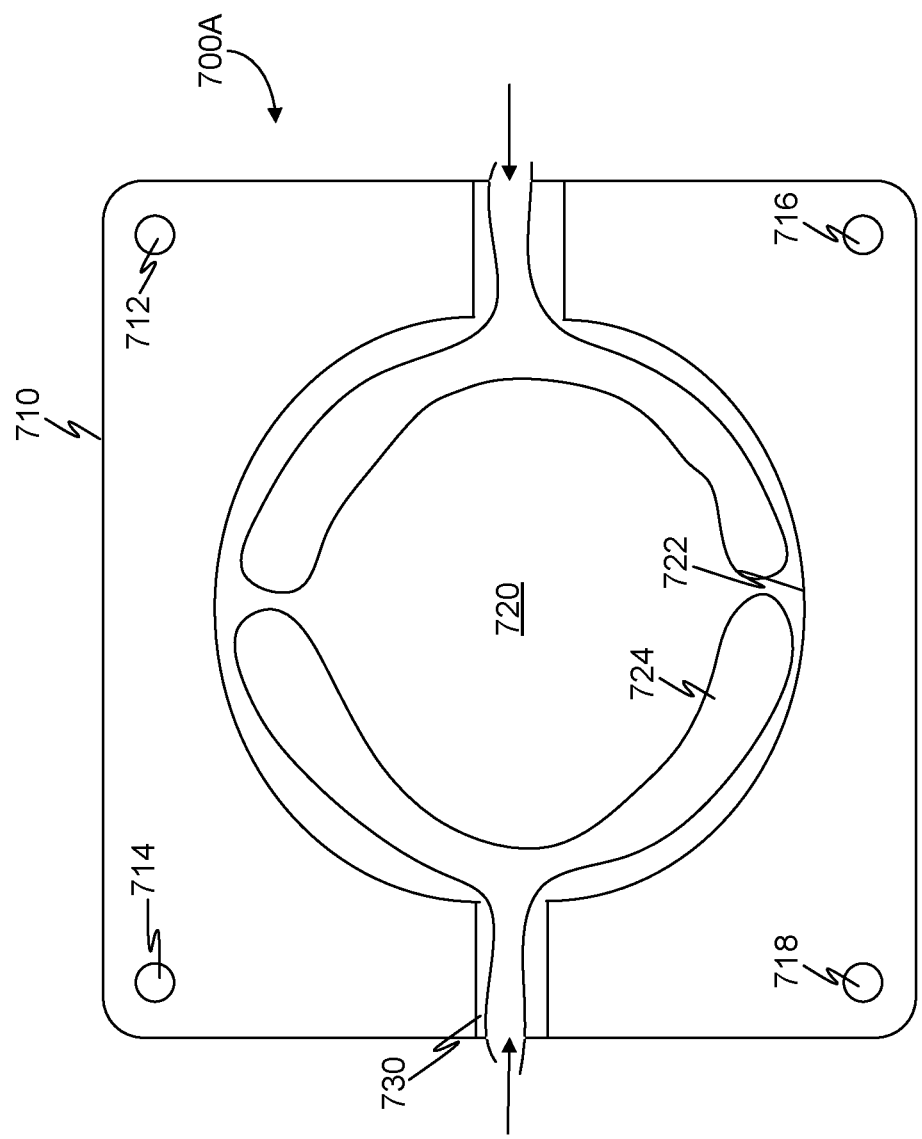
FIG. 7A is a diagram of a cross sectional view of a proximal part, implemented according to an embodiment.

FIG. 7A is an example diagram 700A of a cross sectional view of a proximal part 710, implemented according to an embodiment. A proximal part 710 includes a plurality of perforations for affixing to support rods, for example as explained above. A first perforation 712, second perforation 714, third perforation 716 and fourth perforation 718 correspond respectively to the first perforation 512, second perforation 514, third perforation 516 and fourth perforation 518 of FIG. 5 above. The proximal part 710 further includes an aperture 720 which corresponds to the aperture 520 of FIG. 5. The aperture 720 has an internal surface 722, to which at least an inflatable member, such as inflatable member 724 may be affixed. The inflatable member 724 is connected through a duct 730, corresponding to the duct 530 of FIG. 5, to a pressure supply (not shown), which can supply positive or negative pressure in order to inflate or deflate, respectively, the inflatable member 724. The inflatable member 724 may serve to both hold the phalange in place due to a friction fit, and also center the phalange relative to the aperture 720, which in turn is centered to a pin guide, allowing the k-wire to pass through the distal phalanx.

Figure 7B:
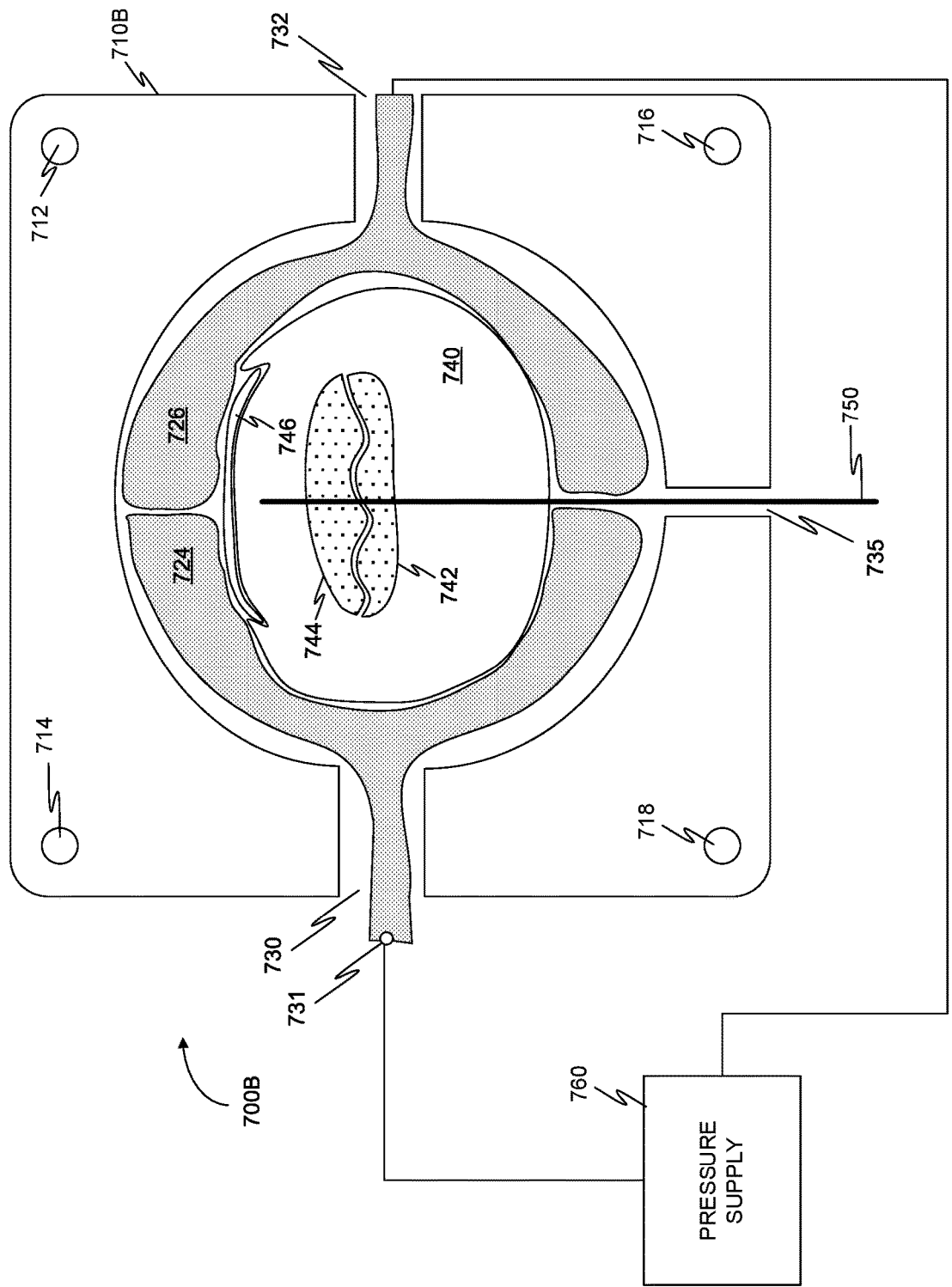
FIG. 7B is a diagram of a cross sectional view of a proximal part, implemented in accordance with another embodiment.

FIG. 7B is an example diagram 700B of a cross sectional view of a proximal part, implemented in accordance with another embodiment. A phalange 740 includes a middle phalanx exhibiting a lateral fracture, such that the middle phalanx is broken into a bottom fragment 742 and a top fragment 744. The phalange is inserted into the proximal part 710B. A first inflatable cushion 724 is inserted so that a connector 731 of the first inflatable cushion 724 is inserted through a duct 730, and connected to a pressure supply 760. The pressure supply 760 supplies pressure to the first inflatable cushion 724 and a second inflatable cushion 726, so that together the inflatable cushions envelop the phalange 740 and hold it in place. The second cushion inflatable cushion 726 is inserted into a second duct 732 to connect to the power supply.

The proximal part 710B may further include a channel 735, through which a k-wire may be placed, to be inserted in the phalange 740 through at least the bottom fragment 742 and the top fragment 744. In certain embodiments, multiple channels may be implemented so that k-wires may be placed at different radial approaches (i.e. different radiant angles with respect to the phalange 740).

In an embodiment, the inflatable cushions may be removed from the proximal part 710B. Removal of the inflatable cushions allows to disinfect the proximal part 710B as it is exposed to a cleaning solution. For example, the proximal part may be submerged into an alcohol solution, or into an aqueous solution in a sonic bath. Alternatively, when applying heat in order to disinfect or sterilize, the ability to remove a cushion may likewise be advantageous. While discussion here is with respect to the proximal part 710B, it should be evident that the teachings may apply to any of the proximal parts, distal parts, or other guide devices disclosed herein.

In certain embodiments, the proximal part, distal part, or other device part, may be implemented using a radiolucent material. A radiolucent material does not absorb x-ray radiation, as opposed to radiopaque materials, such as aluminum, stainless steel, and titanium, which absorb x-ray radiation and therefore obstruct visibility when performing x-ray based imaging. For example, a radiolucent material may be a thermoplastic resin, which is reinforced with carbon fibers. Polyether ether ketone (PEEK) is one such example of a thermoplastic polymer that may be further reinforced using bi-directional carbon fibers. This allows the radiolucent material to withstand use while retaining structural stability after multiple sterilization procedures.

Figure 8A:
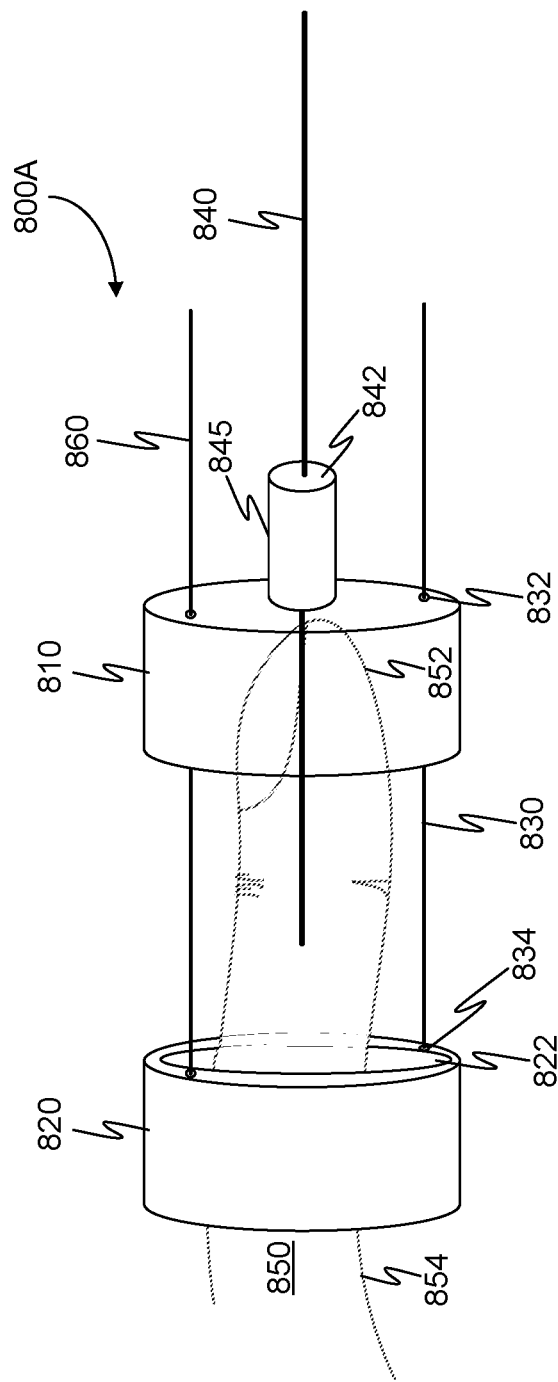
FIG. 8A is a diagram of a side view of a multi-part k-wire guide, implemented in accordance with an embodiment.

FIG. 8A is an example diagram 800A of a side view of a multi-part k-wire guide, implemented in accordance with an embodiment. A multi-part k-wire guide includes a distal part 810 and at least a proximal part 820. In an embodiment, a plurality of proximal parts may be used, spread across a phalange 850. The proximal part 820 is placed such that the phalange 850 extends through an aperture 822 of the proximal part 820. The proximal part 820 may reside at the middle phalanx, proximal phalanx, and both, for example when using a plurality of proximal parts. The proximal part includes a plurality of guide perforations, such as first perforation 834.

The distal part 810 is placed at the distal phalanx 852. The distal part 810 includes a pin guide 845 having an opening 842, through which a k-wire 840 may be placed. The distal part 810 may further include a plurality of guide perforations, such as second perforation 832. The guide perforations are operative to receive through them a guiding rod. For example, guiding rod 830 is inserted through the first perforation 834 and the second perforation 832. In an embodiment a guiding rod may be threaded, and held in place (i.e., affixed to the distal part and the proximal part) using nuts. A second guiding rod 860 is also used to affix the proximal part 820 and the distal part 810. The guiding rods 830 and 860 may be used to ensure that the proximal part 820 and the distal part 810 do not move relative to each other, and that the phalange 850 is centered in the respective apertures therein.

Figure 8B:
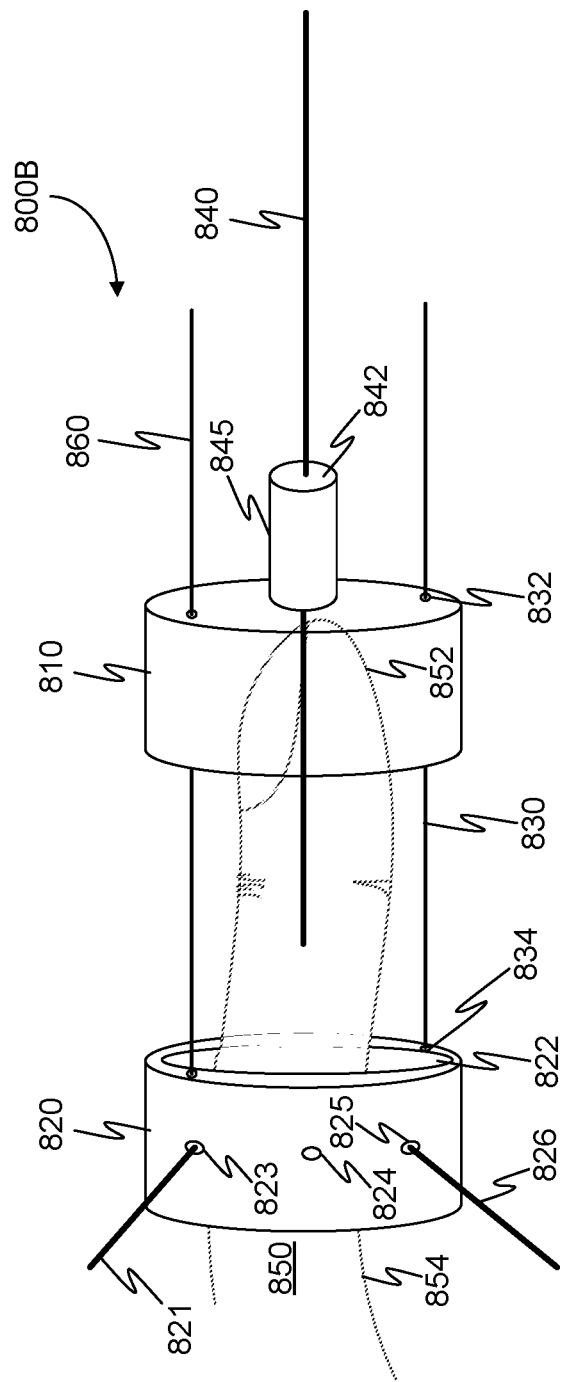
FIG. 8B is a diagram of a side view of a multi-part k-wire guide, implemented in accordance with another embodiment.

FIG. 8B is an example diagram 800B of a side view of a multi-part k-wire guide, implemented in accordance with another embodiment. The proximal part 820 includes a plurality of channels, such as first channel 823, second channel 824 and third channel 825. In an embodiment, one or more k-wires may be inserted through each of the plurality of channels. In some embodiments at least a portion of the plurality of channels may have a diameter which allows the passage of a single k-wire. For example, a first k-wire 821 is inserted into the phalange 850 through the first channel 821. A second k-wire 826 is inserted into the phalange 850 through the third channel 825. In certain embodiments, the distal part 810 may also be implemented with at least a channel (not shown) for inserting at least a k-wire therethrough.

In embodiments where a channel is implemented for inserting a k-wire, a foam based cushion may be used in place of an inflatable cushion. The foam based cushion may be a polyurethane polymer. A foam based cushion may hold a phalange in place with less force than an inflatable cushion due to the difference in applied pressure, however a k-wire may pierce the foam based cushion without affecting performance, while a k-wire piercing an inflatable cushion would render the cushion inoperable in a deflated state.

Figure 8C:
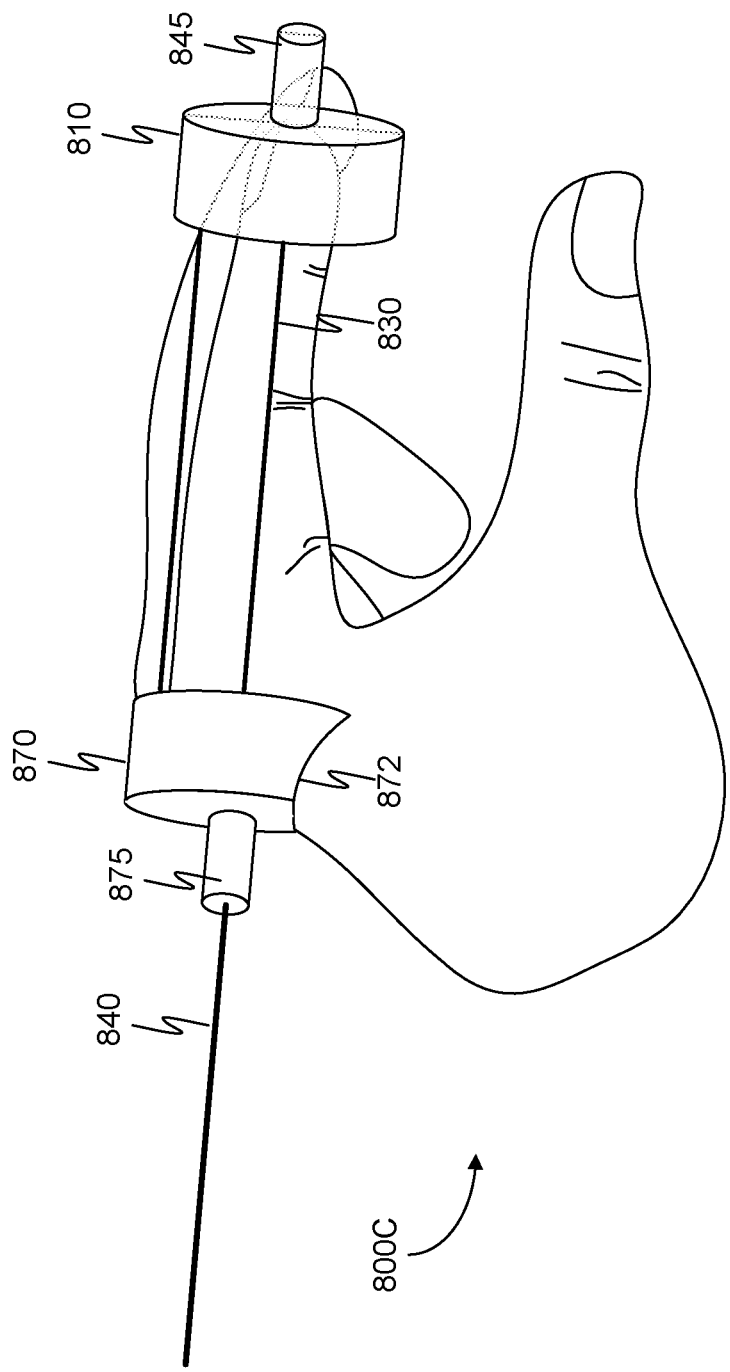
FIG. 8C is a diagram of a side view of a multi-part k-wire guide in a proximal fixation, implemented in accordance with yet another embodiment.

FIG. 8C is an example diagram 800C of a side view of a multi-part k-wire guide in a proximal fixation, implemented in accordance with yet another embodiment. This diagram 800C shows a proximal fixation applied to the index finger of a left hand. In an embodiment, a first distal part 810 includes a pin guide 845. In some embodiments, the first distal part 810 may be implemented without the pin guide 845. This may be beneficial in order to hold in place (i.e., stabilize) a proximal guide 870, which is placed in proximity of the MJP joint. The first distal part 810 may be affixed to one or more guide rods, such as a first guide rod 830. The proximal guide 870 includes a pin guide 875. In an embodiment, one or more k-wires may be inserted through the pin guide 875. In certain embodiments, the proximal guide 870 may include a plurality of pin guides. In some embodiments, a pin guide is centered relative to the MCP joint. A k-wire 840 may be placed through the pin guide 875, and inserted through the MCP joint, and be further inserted at least into the proximal phalanx.

In certain embodiments, the proximal guide 870 may include an indent 872 at a bottom portion (i.e., a portion which is closer to the wrist) in order to accommodate the structure of the MCP joint area. As with the distal guides described above, the proximal guide 870 may include a cushion in order to generate pressure on the phalange and increase friction to prevent movement of the phalange in the proximal guide. In some embodiments, a distal guide such as described above can be utilized as a proximal guide 870 for performing a proximal fixation.

Figure 9:
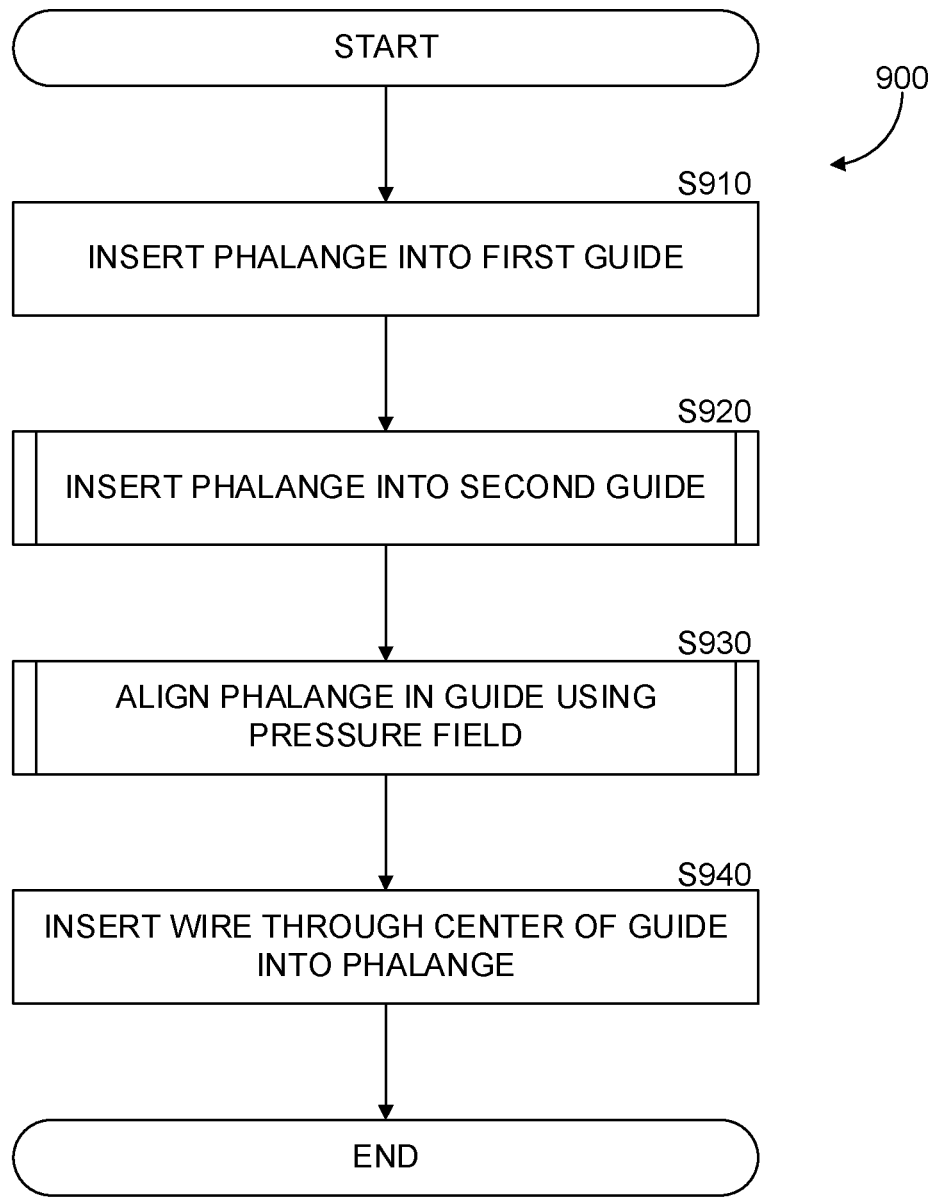
FIG. 9 is a flowchart 900 of a method for performing a k-wire fixation in a phalange using a centered guide, implemented in accordance with an embodiment.

FIG. 9 is an example flowchart 900 of a method for performing a k-wire fixation in a phalange using a centered guide, implemented in accordance with an embodiment.

At S910, a phalange is inserted into a first guide. The first guide includes a pin guide as described in more detail above, through which a k-wire may be inserted. The pin guide is concentrical to an aperture of the first guide. In certain embodiments the distal phalanx is inserted into the aperture of the first guide and held in place such that the lateral midpoint of the distal tip of the phalange is substantially aligned with the center of the aperture, which in turn is concentric to the pin guide, thus ensuring that the k-wire does not slip when inserted into the distal phalanx. In some embodiments the distal phalanx may be held in place by a friction fit created by an inflating member which surrounds at least a first and second portion of the distal phalange. The first guide may be a distal part, such as described in more detail above.

At optional S920, the phalange is inserted into a second guide. When using a second guide, the phalange is inserted first into the second guide, and then into the first guide. For example, a proximal part may be a second guide, and a distal part may be a first guide. In certain embodiments, a plurality of second guides may be used, as needed, in order to provide additional support. The second guide includes an aperture through which the phalange may be inserted, and a plurality of guide perforations, which may each accept a guiding rod, to affix the first guide and the second guide to the guiding rod.

At optional S930, the phalange may be aligned in a guide using a pressure field. In an embodiment the first guide, second guide, or both, may include a pressure field. A pressure field may be generated, for example by an inflating member which applies pressure between an internal surface of the guide and the phalange portion which is inserted therethrough. In an embodiment, each guide may include one or more inflating members, each inflating member controlled by a pressure supply which may supply positive or negative pressure in order to align the phalange. In certain embodiments the phalange should be aligned to the center of a circular aperture of each guide, which in turn are concentric with the pin guide.

At S940, a k-wire is inserted through the pin guide. Inserting the wire through a pin guide ensures that the k-wire does not slip and passes through the distal phalanx in a manner which provides proper alignment. The pin guide is placed such that an opening of the pin guide is substantially aligned with the lateral midpoint of the distal tip of the phalange. In an embodiment, the pin guide opening is further concentric to the aperture of the first guide, the second, or both.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. A guide device for fixation of a fractured phalange by insertion of a k-wire having a diameter, the guide device comprising:
    a distal part, having a first opening of a first diameter at a proximal end of the distal part for inserting at least a portion of the fractured phalange into a tubular section of the distal part, and a second opening at a distal end of the distal part; and
    a pin guide fixedly connected to the distal end of the distal part, the pin guide having a second diameter which is greater than the diameter of the k-wire, and less than the first diameter,
    wherein the pin guide is shaped so as to define an elongate cylindrical guide passage therethrough that is configured to align the k-wire with the portion of the fractured phalange during the insertion of the k-wire into the portion of the fractured phalange while the portion of the fractured phalange is held in place within the tubular section of the distal part.

2. The guide device of claim 1, further comprising a proximal part, the proximal part comprising:
    an aperture for inserting the fractured phalange; and
    a plurality of fasteners, for fastening the proximal part to the distal part.

3. The guide device of claim 2, further comprising:
    at least a cushion, wherein the at least a cushion is located in any one of: the tubular section of the distal part, and the aperture.

4. The guide device of claim 3, wherein the at least a cushion is selected from the group consisting of: a sponge cushion, and an inflatable cushion.

5. The guide device of claim 4, wherein the at least a cushion comprises the inflatable cushion, and wherein the distal part or the proximal part is shaped so as to define a duct through which the inflatable cushion is inflatable.

6. The guide device of claim 2, comprising a plurality of pin guides including the pin guide that is fixedly connected to the distal end of the distal part.

7. The guide device of claim 6, for use with first and second k-wires, wherein at least a first pin guide of the plurality of pin guides is at an angle relative to at least another pin guide of the plurality of pin guides, such that the first pin guide orients the first k-wire, when inserted through the first pin guide, in a direction not parallel to a direction that the at least another pin guide orients the second k-wire, when inserted through the at least another pin guide.

8. The guide device of claim 2, further comprising:
    a plurality of rods, each rod coupled to a fastener of the plurality of fasteners.

9. The guide device of claim 1,
    wherein the k-wire is a first k-wire, and wherein the guide device is for use with the first k-wire and a second k-wire, and
    wherein an element of the guide device is shaped as to define at least a channel, configured for inserting therethrough the second k-wire to guide the second k-wire into the fractured phalange by a lateral approach, the element selected from the group of elements consisting of: the proximal part and the distal part.

10. The guide device of claim 9, for use with the first k-wire, the second k-wire, and a third k-wire,
    wherein the channel is a first channel and the lateral approach is a first lateral approach, and
    wherein the selected element of the guide device is shaped so as to define at least a second channel, configured for inserting therethrough the third k-wire into the fractured phalange by a second lateral approach oriented with respect to the fractured phalange differently from an orientation of the first lateral approach.

11. The guide device of claim 1, wherein the pin guide is concentric to the tubular section.

12. The guide device of claim 1, wherein a diameter of the pin guide is 1 millimeter, with a 5% threshold.

13. The guide device of claim 1,
    wherein the pin guide is a first pin guide and the elongate cylindrical guide passage is a first elongate cylindrical guide passage, and
    wherein the guide device further comprises:
        a proximal part, which is separate from and coupled to the distal part; and
        a second pin guide fixedly connected to the proximal part, the second pin guide shaped so as to define a second elongate cylindrical guide passage therethrough that is configured to align the k-wire with the fractured phalange during the insertion of the k-wire into the portion of the fractured phalange while the portion of the fractured phalange is held in place within the tubular section of the distal part.

14. The guide device of claim 13, wherein the proximal part is shaped so as to define a partial ring.

15. A kit comprising the guide device of claim 1, the kit further comprising the k-wire.

16. A method for performing k-wire fixation of a fractured phalange, the method comprising:
    inserting at least a portion of the fractured phalange into a tubular section of a distal part via a first opening at a proximal end of the distal part, the distal part including a pin guide fixedly connected to a distal end of the distal part; and
    fixating the fractured phalange by inserting a k-wire through an elongate cylindrical guide passage of the pin guide and into the fractured phalange, while the elongate cylindrical guide passage aligns the k-wire with the at least a portion of the fractured phalange held in place within the tubular section of the distal part.

17. The method of claim 16, further comprising, before inserting the at least a portion of the fractured phalange into the tubular section of the distal part, inserting the fractured phalange into an aperture of a proximal part.

18. The method of claim 17, further comprising:
    aligning the fractured phalange in the first proximal part and the second proximal distal part using pressure.

19. The method of claim 18, wherein aligning the proximal and the distal parts using the pressure comprises generating the pressure using any of: an inflatable cushion, a sponge cushion, and a combination thereof.

20. The method of claim 17, further comprising:
coupling the proximal part to the distal part using a plurality of rods.

* * * * *